US012186295B2

(12) United States Patent
Pilotaz et al.

(10) Patent No.: US 12,186,295 B2
(45) Date of Patent: *Jan. 7, 2025

(54) OPHTHALMIC COMPOSITIONS CONTAINING A NITRIC OXIDE RELEASING PROSTAMIDE

(71) Applicant: NICOX S.A., Valbonne (FR)

(72) Inventors: Frédéric Pilotaz, Nice (FR); Alan L. Weiner, McKinney, TX (US); Marina Do, Menton (FR); Julien Saldo, Cagnes sur Mer (FR)

(73) Assignee: NICOX S.A., Valbonne (FR)

( * ) Notice: Subject to any disclaimer, the term of this patent is extended or adjusted under 35 U.S.C. 154(b) by 674 days.

This patent is subject to a terminal disclaimer.

(21) Appl. No.: 17/146,057

(22) Filed: Jan. 11, 2021

(65) Prior Publication Data

US 2021/0128458 A1    May 6, 2021

Related U.S. Application Data

(63) Continuation-in-part of application No. PCT/EP2019/068511, filed on Jul. 10, 2019.

(30) Foreign Application Priority Data

Jul. 12, 2018 (EP) .................................. 18290082

(51) Int. Cl.

| | |
|---|---|
| A61K 47/02 | (2006.01) |
| A61K 9/00 | (2006.01) |
| A61K 9/08 | (2006.01) |
| A61K 31/216 | (2006.01) |
| A61K 31/222 | (2006.01) |
| A61K 47/10 | (2017.01) |
| A61K 47/12 | (2006.01) |
| A61K 47/18 | (2017.01) |
| A61K 47/24 | (2006.01) |
| A61K 47/26 | (2006.01) |

(52) U.S. Cl.
CPC .......... *A61K 31/216* (2013.01); *A61K 9/0048* (2013.01); *A61K 9/08* (2013.01); *A61K 31/222* (2013.01); *A61K 47/02* (2013.01); *A61K 47/10* (2013.01); *A61K 47/12* (2013.01); *A61K 47/18* (2013.01); *A61K 47/183* (2013.01); *A61K 47/186* (2013.01); *A61K 47/24* (2013.01); *A61K 47/26* (2013.01)

(58) Field of Classification Search
CPC ...... A61K 31/216; A61K 9/0048; A61K 9/08; A61K 31/222; A61K 47/02; A61K 47/10; A61K 47/12; A61K 47/18; A61K 47/183; A61K 47/186; A61K 47/24; A61K 47/26; A61K 31/5575; A61K 47/14; A61K 47/38; A61P 27/06; A61P 27/02
See application file for complete search history.

(56) References Cited

U.S. PATENT DOCUMENTS

| | | | |
|---|---|---|---|
| 8,637,054 B2 | 1/2014 | Mercier | |
| 8,772,337 B2 | 7/2014 | Pilotaz et al. | |
| 8,795,634 B2 | 8/2014 | Illum et al. | |
| 10,688,073 B2 * | 6/2020 | Pilotaz | A61K 9/0048 |
| 2010/0210720 A1 | 8/2010 | Pilotaz et al. | |
| 2013/0005665 A1 | 1/2013 | Gore et al. | |
| 2013/0267591 A1 | 10/2013 | Khopade et al. | |
| 2015/0080355 A1 | 3/2015 | Malhotra et al. | |

FOREIGN PATENT DOCUMENTS

| | | |
|---|---|---|
| CN | 101835473 A | 9/2010 |
| CN | 102099330 A | 6/2011 |
| CN | 102970973 A | 3/2013 |
| CN | 103764120 A | 4/2014 |
| CN | 104274396 A | 1/2015 |
| CN | 105012231 A | 11/2015 |
| CN | 105380901 A | 3/2016 |
| JP | 2011-508724 A | 3/2011 |
| JP | 2011-519910 A | 7/2011 |
| JP | 2014-522849 A | 9/2014 |
| WO | 2009/013435 A2 | 1/2009 |
| WO | 2009/084021 A2 | 7/2009 |
| WO | 2009136281 A1 | 11/2009 |
| WO | 2012/001009 A1 | 1/2012 |
| WO | 2013003827 A2 | 1/2013 |
| WO | 2013/017821 A1 | 2/2013 |

OTHER PUBLICATIONS

International Search Report and Written Opinion issued in corresponding International Application No. PCT/EP2019/068511 dated Oct. 21, 2019.
Impagnatiello, Francesco, et al., "Prostaglandin analogues and nitric oxide contribution in the of ocular hypertension and glaucoma (Review Article)", British Journal of Pharmacology, Wiley-Blackwell, UK, Apr. 18, 2018 (Apr. 18, 2018) pp. 1-11.
Chinese Office Action issued in corresponding Chinese Application No. 201910622356.1 mailed on Dec. 28, 2020, 16 pages (8 pages of English Translation and 8 pages of Original Document).
EPO Search Report Communication of 18290082.9-1114 mailed Jan. 16, 2019.
Impagnatiello et al., "Intraocular Pressure-Lowering Activity of NCX 470, a Novel Nitric Oxide-Donating Bimatoprost in Preclinical Models", Invest Ophthalmol Vis Sci, Oct. 2015, vol. 56, No. 11, pp. 6558-6564.
Zhou., "Micelle carriers based on macrogol 15 hydroxystearate for ocular delivery of terbinafine hydrochloride: In vitro characterization and in vivo permeation", European Journal of Pharmaceutical Sciences, vol. 109, Nov. 15, 2017, pp. 288-296.

* cited by examiner

*Primary Examiner* — Jeffrey S Lundgren
*Assistant Examiner* — Alexander K. Showalter
(74) *Attorney, Agent, or Firm* — ArentFox Schiff LLP

(57) ABSTRACT

The present invention provides aqueous ophthalmic compositions in the form of solution comprising hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester and macrogol 15 hydroxystearate as the only solubilizing agent, and a method for their preparation.

19 Claims, No Drawings

OPHTHALMIC COMPOSITIONS CONTAINING A NITRIC OXIDE RELEASING PROSTAMIDE

This application is a Continuation-In-Part of PCT Application No. PCT/EP2019/068511, filed Jul. 11, 2019, which claims priority to EP Application No. 18290082.9 filed Jul. 12, 2018, the disclosures of which are hereby incorporated by reference in their entireties.

The invention relates to aqueous ophthalmic compositions in the form of solution comprising hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester as active ingredient and macrogol 15 hydroxystearate.

Hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester has the following formula (I)

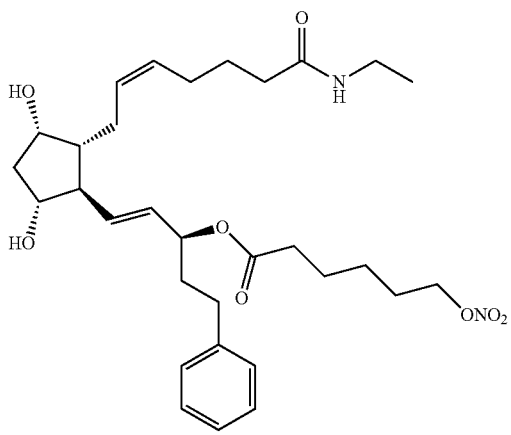

(I)

NCX 470

The compound has shown to be effective as intra ocular pressure (IOP)-lowering agent (F. Impagnatiello, C. B. Toris, M. Batugo, G. Prasanna, V. Borghi, E. Bastia, E. Ongini, A. H. P. Krauss; Invest Ophthalmol Vis Sci. 2015; 56:6558-64). WO 2009/136281 (Nicox SA) discloses the use of Hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester for treating glaucoma and ocular hypertension.

Impagnatiello Francesco et al; British Journal of Pharmacology (2018), pages 1-11 discloses non-clinical pharmacological studies showing the greater IOP-lowering efficacy of NCX 470 than that of equimolar doses of bimatoprost. Both compounds were dissolved in a vehicle containing 0.25% Tween 80, 0.02% BAK, 2% glycerine and 0.1% EDTA.

Topical instillation is the most widely preferred non-invasive route of drug administration for treating elevated intraocular pressure. Most of the conventional dosage forms of the marketed IOP-lowering drugs are eye-drops in the form of aqueous solution, nonetheless the ocular bioavailability of the active principle is very low with topical drop administration. Numerous anatomical and physiological factors limit the ocular absorption of topically applied ophthalmic drugs such as rapid precorneal drug elimination due to solution drainage and systemic absorption from the conjunctival sac and the corneal epithelial barrier. An important target of pharmaceutical formulations is to enable the IOP-lowering drug to penetrate inside the eye after either a unique or multiple topical drops instillations. It is known that the ocular residence time of a drug at the ocular surface is very short after a single drop application. As a result, several formulation approaches are generally used for providing more opportunities to the drug penetrating inside the eye after an application at the ocular surface, and ideally with the lowest dose regimen like once a day, in order to foster patient treatment adherence.

One approach is to increase the ophthalmic solution viscosity. As a result, the solution will have a better adherence to the ocular surface and increasing the ocular residence time of the drug at this side accordingly. As a result, an increase amount of the drug is supposed to penetrate inside the eye. For example, WO 2012/001009 discloses a delivery system consisting in a gelling system based on the combination of two gelling agents to obtain a non-viscous polymeric delivery system that ensures the desired level of viscosity and to potentiate the solubility of the active ingredient, prostaglandin.

Another approach is to leverage an ocular penetration enhancing agent. One of the most famous penetration enhancer is the benzalkonium chloride (BAK). In the field of the prostaglandin ophthalmic formulation, this approach has been leveraged by Allergan with their product Lumigan®. A first product generation has been commercialized where the Bimatoprost prostaglandin was formulated at the 0.03% dose. In this product, the benzalkonium chloride dose was 0.005%. This benzalkonium chloride dose was mainly used for ensuring the antimicrobial protection of the solution. Some year later, a second generation of the Lumigan® has been commercialized with the same efficacy of the old product generation. This new formulation has a lower concentration of bimatoprost (0.01%) but has a 4-fold increase in the amount of benzalkonium chloride (0.02%) compared to the original formulation (0.005%).

Another technical challenge of the ophthalmic pharmaceutical formulations is to stabilize the active principle. It can be noted that some eye drop formulations require cold storage to preserve their active ingredient level, thereby entailing drawbacks of poor usability; for example, for multi-dose bottles the content of active ingredient may decrease during the time if the preparation is not properly stored at a low temperature. Eye drops for the treatment of glaucoma or ocular hypertension are often prescribed for aged persons who could have difficulties to apply the "cold" requirement for drug storage.

U.S. Pat. No. 8,772,337 (Thea Laboratories) discloses ophthalmic solutions stable at room temperature containing a prostaglandin and Solutol® HS15 (macrogol 15-hydroxystearate) without an antimicrobial preservative.

U.S. Pat. No. 8,772,337 discloses that Solutol® HS15 is able to solubilize some prostaglandins like Latanoprost and confers stability at ambient temperature of the solution in absence of quaternary ammonium agent, like benzalkonium chloride, used there as the usual solubilizer for such a prostaglandin analog. More specifically, it confers prostaglandin analog solution stability to the packaging, in particular to LDPE type plastic packaging of European Pharmacopoeia (EP) quality. Therefore Solutol® HS15 can be used as an alternative to polysorbate 80 as solubilizing agent.

The test examples of U.S. Pat. No. 8,772,337 discloses ophthalmic "vehicles" containing Solutol® HS15 (0.5%), phosphate buffer, sorbitol and EDTA.

WO2013/003827 (Allergan) discloses formulations containing macrogol 15-hydroxystearate and a preservative agent. This patent application discloses that the use of macrogol 15-hydroxystearate (Solutol® HS15) as surfactant in place of polyethoxylated surfactants (polysorbate 80/Tween® 80) has several advantages such as solubility enhancement of the API, improved stability of APIs susceptible to degradation by oxidation mechanisms, improved preservative effectiveness of benzalkonium chloride, improved tolerability for ophthalmic use.

WO 2009/084021 (Sun Pharmaceutical) discloses that the addition of a stabilizing amount of polyglycol ester of 12-hydroxystearic acid (Solutol® HS15) to an ophthalmic composition comprising one or more prostaglandin derivatives reduces the sorption of the prostaglandin derivatives to the polyethylene containers and that the addition of a small amount of oil further reduces the sorption of prostaglandin derivatives onto the low density polyethylene containers.

U.S. Pat. No. 8,795,634 (Critical Pharma.) discloses the use of Solutol® HS15 as absorption enhancer to improve the systemic absorption of topically applied therapeutic agents through the mucosal membranes of the nasal cavity, buccal cavity and respiratory tract. However the mechanisms of the adsorption of an active principle applied topically to mucosal membranes are different from the pathway employed by a therapeutic agent applied topically to cross the eye; indeed the therapeutic agent must cross anatomical barriers that are inherent and unique to ocular anatomy (i.e. cornea epithelium, conjunctiva and sclera) and bypass protective mechanisms of the eye (i.e. blinking, tear film turnover and drainage).

Macrogol 15 hydroxystearate (Kolliphor® HS15, from BASF, formerly known as Solutol® HS15) is the main excipient of the formulation of the present invention; as reported above, there are several prior art documents that discloses the use of macrogol 15 hydroxystearate as excipient for ophthalmic composition.

The term "macrogol 15 hydroxystearate" refers to a mixture of mainly monoesters and diesters of 12-hydroxystearic acid and macrogols obtained by the ethoxylation of 12-hydroxystearic acid. Macrogol 15 hydroxystearate is also known as 12-hydroxystearic acid polyethylene glycol copolymer, polyethylene glycol-15-hydroxystearate and polyethylene glycol 660 12-hydroxystearate. USP-NF listed this compound as Polyoxyl 15 hydroxystearate too.

As reported above, several prior art documents disclose the use of macrogol 15 hydroxystearate as excipient for ophthalmic compositions, however, as per today, there is only one eyedrop approved in Europe including macrogol 15 hydroxystearate and a prostaglandin analog. This drug has been registered by Rafarm S.A under the name of Provastor® and it contains Travoprost as a prostaglandin analog and BAK as antimicrobial preservative system.

Hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester is a viscous oil having a minimum aqueous solubility of 0.02 mg/ml therefore aqueous pharmaceutical compositions of hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester must contain solubilizing agents that increase the water solubility of the compound and allow achieving therapeutically active concentrations of the compound.

WO 2009/136281 discloses a formulation containing hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester in a vehicle comprising polysorbate 80 (Tween® 80) 0.5%, benzalkonium chloride 0.02%, citrate buffer, water and having pH 5.5.

Polysorbate 80 has been extensively used as excipient for ophthalmic compositions. For example, the product Rescula®, sold by Novartis, combines unoprostone with a mixture of benzalkonium chloride and polysorbate 80 at 0.015% by weight of the solution.

The present invention relates to an ophthalmic aqueous composition in the form of solution comprising hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester, and macrogol 15 hydroxystearate, wherein macrogol 15 hydroxystearate is preferably the only solubilizing agent.

The ophthalmic aqueous compositions of the invention provide a higher ocular permeability of the active principle hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester compared to known formulation, so allowing an enhanced ocular absorption of the therapeutic active compound.

The invention also provides ophthalmic aqueous compositions in the form of solutions comprising hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester that are both chemically and physically stable on storage at room temperature.

SUMMARY OF THE INVENTION

The present invention provides an ophthalmic aqueous composition in the form of solution comprising 0.005% to 0.18% w/w hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester, from 0.5% w/w to 1.5% w/w macrogol 15 hydroxystearate, wherein macrogol 15 hydroxystearate is preferably the only solubilizing agent.

Another embodiment is an ophthalmic aqueous composition in the form of solution comprising 0.005% to 0.10% w/w hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester, from 0.5% w/w to 1.5% w/w macrogol 15 hydroxystearate, wherein macrogol 15 hydroxystearate is preferably the only solubilizing agent.

A preferred embodiment of the present invention provides an ophthalmic aqueous composition in the form of solution comprising from 0.005% w/w to 0.065% w/w hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester, from 0.5% w/w to 1.5% w/w macrogol 15 hydroxystearate and a pharmaceutically acceptable aqueous vehicle, wherein macrogol 15 hydroxystearate is preferably the only solubilizing agent.

In the field of ophthalmology, and in particular in aqueous ophthalmic compositions, solubilizing agents are compounds which improve the dissolution of a biologically active component with relatively low water solubility.

Preferably the amount of hexanoic acid, 6-(nitrooxy)-, (1S,2E)-3-[(1R,2R,3S,5R)-2-[(2Z)-7-(ethylamino)-7-oxo-2-hepten-1-yl]-3,5- dihydroxycyclopentyl]-1-(2-phenylethyl)-

2-propen-1-yl ester in the ophthalmic solution is from 0.01% w/w to 0.065% w/w, most preferably is 0.021% w/w, 0.042% w/w or 0.065% w/w.

The ophthalmic aqueous solution may contain benzalkonium chloride (BAK) as antimicrobial preservative agent in an amount from 0.013% w/w to 0.02% w/w and an edetate salt (EDTA), such as ethylenediaminetetraacetic acid disodium salt, in an amount from 0.03% w/w to 0.07% w/w as antimicrobial preservative aid agent; preferably the amount of benzalkonium chloride (BAK) is from 0.013% w/w to 0.02% w/w and the amount of the edetate salt (EDTA) is 0.05% w/w; most preferably the amount of benzalkonium chloride (BAK) is 0.016% w/w and the amount of the edetate salt (EDTA) is 0.05% w/w.

The aqueous ophthalmic composition of the invention further includes a buffer selected from: sodium dihydrogen phosphate, disodium hydrogen phosphate heptahydrate, potassium dihydrogen phosphate, or dipotassium hydrogen phosphate, boric acid and salts thereof, acetates such as sodium acetate and mixtures thereof preferably. Preferably, the buffer of the aqueous ophthalmic composition of the invention is a mixture of sodium phosphate dibasic heptahydrate and boric acid or a mixture of citric acid and sodium phosphate dibasic heptahydrate. The preferred pH for the formulation is 6.0. This pH has been found as being the optimal pH for enabling both a suitable formulation stability over long term storage conditions and an appropriate ocular tolerance when formulations are delivered on the eye surface.

The pH of the aqueous ophthalmic composition is adjusted preferably in a range of from 5.5 to 6.5, more preferably at pH 6.0.

The aqueous ophthalmic composition of the invention may include a pH-adjusting agent selected from hydrochloric acid, citric acid, phosphoric acid, acetic acid, tartaric acid, sodium hydroxide, potassium hydroxide, sodium carbonate, and sodium bicarbonate; preferably the aqueous ophthalmic composition of the invention contains hydrochloric acid and or sodium hydroxide in an amount to adjust the pH in a range from 5.5 to 6.5; more preferably at pH 6.0.

The ophthalmic aqueous solution may contain tonicity agents used for adjusting the osmolality of the formulation and targeting required isotonicity. Preferred tonicity agents are sodium chloride, sorbitol, glycerin (or glycerol) and mannitol. Isotonicity is set-up at 300 mOsm/kg, but a broader range of 260 to 340 mOsm/kg is usually acceptable for formulating ophthalmic solutions. Preferably, osmolality of the solution is within the range of 280 to 320 mOsm/kg.

The ophthalmic aqueous solution of the invention may contain a viscosity-adjusting agent used for improving the contact between the solution and the eye and fostering an improved spreading of the product on the ocular surface. Preferred viscosity-adjusting agents are cellulose derivative polymers like carboxymethyl cellulose or hydroxypropyl methyl cellulose, hyaluronic acid, polyvinyl alcohol, carboxylic acid polymers like carbomers or polycarbophils. Most preferably, the viscosity-adjusting agent is hydroxypropyl methyl cellulose at a concentration less than 0.5% w/w. The viscosity of the ophthalmic aqueous solution is adjusted between 5 and 10 m·Pa·s for Newtonian solutions when using cellulose derivatives, but can be higher with high viscosity solution with non-Newtonian/pseudoplastic rheological behaviors, typically obtained when using carboxylic polymers.

Another embodiment of the invention provides an ophthalmic aqueous composition in the form of solution comprising 0.005% w/w to 0.10% w/w hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester, 0.5% w/w to 1.5% w/w macrogol 15 hydroxystearate, 0.013% w/w to 0.02% w/w benzalkonium chloride, 0.03% w/w to 0.07% w/w ethylenediaminetetraacetic acid disodium salt dihydrate, sodium phosphate dibasic heptahydrate and boric acid and water, wherein the pH of the ophthalmic solution is 6 and wherein macrogol 15 hydroxystearate is the only solubilizing agent.

Another embodiment of the invention provides an ophthalmic aqueous composition in the form of solution comprising 0.005% w/w to 0.065% w/w hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester, 0.5% w/w to 1.5% w/w macrogol 15 hydroxystearate, 0.013% w/w to 0.02% w/w benzalkonium chloride, 0.03% w/w to 0.07% w/w ethylenediaminetetraacetic acid disodium salt dihydrate, sodium phosphate dibasic heptahydrate and boric acid and water, wherein the pH of the ophthalmic solution is 6 and wherein macrogol 15 hydroxystearate is the only solubilizing agent; preferably the amount of hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester in the ophthalmic solution is from 0.01% w/w to 0.065% w/w, most preferably is 0.042% w/w, 0.021% w/w or 0.065% w/w; optionally the ophthalmic solution further comprises HCl 1.2 M/NaOH 1M to adjust the pH to pH 6.0.

Another embodiment of the invention provides an ophthalmic aqueous composition in the form of solution comprising 0.005% w/w to 0.10% w/w hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester, 1.0% w/w macrogol 15 hydroxystearate, 0.016% w/w benzalkonium chloride, 0.05% w/w ethylenediaminetetraacetic acid disodium salt dihydrate, sodium phosphate dibasic heptahydrate and boric acid and water, wherein the pH of the ophthalmic solution is 6 and wherein macrogol 15 hydroxystearate is the only solubilizing agent.

Another embodiment of the invention provides an ophthalmic aqueous composition in the form of solution comprising 0.005% w/w to 0.065% w/w hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-ylester, 1.0% w/w macrogol hydroxystearate, 0.016% w/w benzalkonium chloride, 0.05% w/w ethylenediaminetetraacetic acid disodium salt dihydrate, sodium phosphate dibasic heptahydrate and boric acid and water, wherein the pH of the ophthalmic solution is 6 and wherein macrogol 15 hydroxystearate is the only solubilizing agent; preferably the amount of hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester in the ophthalmic solution is 0.01% w/w to 0.065% w/w, most preferably is 0.042% w/w, 0.021% w/w or 0.065% w/w; optionally the ophthalmic solution further comprises HCl 1.2 M/NaOH 1M to adjust the pH to pH 6.0.

Another embodiment of the invention provides an ophthalmic aqueous composition in the form of solution consisting of: 0.005% w/w to 0.10% w/w hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester, 1.0% to 1.5% w/w macrogol 15 hydroxystearate, 0.016% w/w benzalkonium chloride, 0.05% w/w ethylenediaminetetraacetic acid disodium salt dihydrate, 2.76% w/w sorbitol, 1.33% w/w sodium phosphate dibasic heptahydrate (Na$_2$HPO$_4$ 7H$_2$O), 0.5% w/w boric acid and water, wherein the pH of the ophthalmic solution is 6 and wherein macrogol 15 hydroxystearate is the only solubilizing agent.

Another embodiment of the invention provides an ophthalmic aqueous composition in the form of solution consisting of: 0.005% w/w to 0.065% w/w hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-ylester, 1.0% w/w macrogol hydroxystearate, 0.016% w/w benzalkonium chloride, 0.05% w/w ethylenediaminetetraacetic acid disodium salt dihydrate, 2.76% w/w sorbitol, 1.33% w/w sodium phosphate dibasic heptahydrate (Na$_2$HPO$_4$ 7H$_2$O), 0.5% w/w boric acid and water, wherein the pH of the ophthalmic solution is 6 and wherein macrogol 15 hydroxystearate is the only solubilizing agent; preferably the amount of hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester in the ophthalmic solution is from 0.01% w/w to 0.065% w/w, most preferably is 0.021% w/w, 0.042% w/w or 0.065% w/w; optionally the ophthalmic solution further comprises HCl 1.2 M/NaOH 1M to adjust the pH to pH 6.0.

Specific examples of the ophthalmic aqueous composition in the form of solution of the invention are:

0.042% w/w hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester, 1.0% w/w macrogol 15 hydroxystearate, 0.016% w/w benzalkonium chloride, 0.05% w/w ethylenediaminetetraacetic acid disodium salt dihydrate, 2.76% w/w sorbitol, 1.33% w/w sodium phosphate dibasic heptahydrate, 0.5% w/w boric acid and water and having pH 6;

0.021% w/w hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester, 1.0% w/w macrogol 15 hydroxystearate, 0.016% w/w benzalkonium chloride, 0.05% w/w ethylenediaminetetraacetic acid disodium salt dihydrate, 2.76% w/w sorbitol, 1.33% w/w sodium phosphate dibasic heptahydrate, 0.5% w/w boric acid and water and water and having pH 6;

0.065% w/w hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester, 1.0% w/w macrogol 15 hydroxystearate, 0.016% w/w benzalkonium chloride, 0.05% w/w ethylenediaminetetraacetic acid disodium salt dihydrate, 2.76% w/w sorbitol, 1.33% w/w sodium phosphate dibasic heptahydrate, 0.5% w/w boric acid and water and having pH 6;

0.10% w/w hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester, 1.5% w/w macrogol 15 hydroxystearate, 0.016% w/w benzalkonium chloride, 0.05% w/w ethylenediaminetetraacetic acid disodium salt dihydrate, 0.52% w/w glycerol, 2.33% w/w sodium phosphate dibasic heptahydrate, 0.36% w/w citric acid and water and having pH 6.

In the above ophthalmic aqueous compositions hydrochloride acid or sodium hydroxide may be used as pH adjusting agents.

The above reported ophthalmic aqueous solutions may be packaged in low density polyethylene (LDPE) primary containers, usually a multidose ophthalmic bottles with cap an dropper tip enabling to deliver calibrated drops with a controlled drop size. Example of such primary containers can be Rispharm® bottles from Berry-Plastics, Boston Round® from Amcor, 3 pieces bottles from either Gerresheimer, Philips-Medisize, Bormioli or equivalent.

The ophthalmic aqueous composition in the form of solution may be provided as anti-microbial preservative free ophthalmic aqueous solutions.

An embodiment of the invention provides an anti-microbial preservative free ophthalmic aqueous composition in the form of solution comprising 0.005% w/w to 0.10% w/w hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester, 0.5% w/w to 1.5% w/w macrogol 15 hydroxystearate, sodium phosphate dibasic heptahydrate and boric acid and water, wherein the pH of the ophthalmic solution is 6, further comprising a tonicity agent and optionally a further pH-adjusting agent, wherein macrogol 15 hydroxystearate is the only solubilizing agent.

A specific example of preservative free ophthalmic aqueous composition in the form of solution is the following composition consisting of: 0.042% w/w hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester, 1.0% w/w macrogol 15 hydroxystearate, 2.76% w/w sorbitol, 1.33% w/w sodium phosphate dibasic heptahydrate, 0.5% w/w boric acid and water and having pH 6.

Other specific examples of preservative free ophthalmic aqueous composition in the form of solution are the following compositions:

0.042% w/w hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester, 1.0% w/w macrogol 15 hydroxystearate, 2.76% w/w sorbitol, 1.33% w/w sodium phosphate dibasic heptahydrate, 0.5% w/w boric acid and water and having pH 6.

0.021% w/w hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester, 1.0% w/w macrogol 15 hydroxystearate, 2.76% w/w sorbitol, 1.33% w/w sodium phosphate dibasic heptahydrate, 0.5% w/w boric acid and water and having pH 6.

0.065% w/w hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester, 1.0% w/w macrogol 15 hydroxystearate, 2.76% w/w sorbitol, 1.33% w/w sodium phosphate dibasic heptahydrate, 0.5% w/w boric acid and water and having pH 6.

0.10% w/w hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester, 1.5% w/w macrogol 15 hydroxystearate, 0.52% w/w glycerol, 2.33% w/w sodium phosphate dibasic heptahydrate, 0.36% w/w citric acid and water and having pH 6.

In the above ophthalmic aqueous compositions hydrochloride acid or sodium hydroxide may be used as pH adjusting agents.

The antimicrobial preservative free ophthalmic aqueous compositions of the invention are packaged in containers that prevent microbial contamination of the formulations even after multiple uses or the antimicrobial preservative free ophthalmic aqueous compositions are packaged in unit dose containers which are sterile in the unopened form.

Such antimicrobial preservative free formula can be packaged either in a single-dose or unit dose LDPE primary packaging or inside a preservative free multidose container system.

Usually, the preservative free ophthalmic aqueous compositions of the invention are packed in monodose containers intended for single-use by the patient. In another embodiment, the antimicrobial preservative free ophthalmic aqueous compositions of the invention are packed in preservative free multidose containers that enable the formulation to be kept germ-free even after multiple uses by the patient. Examples of preservative free multidose containers are: OSD® from Aptar, Novelia® from Nemera, 3K® from Aeropump, or equivalent devices).

The macrogol 15 hydroxystearate used in the invention is the commercially available Kolliphor® HS15, formerly known as Solutol® HS15 and listed at the USP as polyoxyl-15 hydroxystearate too; it consists of polyglycol mono- and di-esters of 12-hydroxystearic acid and of about 30% of free polyethylene glycol.

The aqueous ophthalmic compositions in the form of solution of the invention showed efficacy in reducing intraocular pressure, therefore they may be used in the treatment of ocular hypertension, glaucoma or in a method of reducing intraocular pressure.

Another object of the invention relates to an ophthalmic aqueous composition in the form of solution according to the invention for use in the treatment of ocular hypertension, glaucoma or in a method of reducing intraocular pressure.

Another object of the invention relates to the above defined ophthalmic aqueous compositions in the form of solution for use in the treatment of ocular hypertension, glaucoma or for reducing intraocular pressure.

Another embodiment of the invention relates to an ophthalmic aqueous composition in the form of solution comprising 0.005% to 0.18% w/w hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester, from 0.5% w/w to 1.5% w/w macrogol 15 hydroxystearate wherein macrogol 15 hydroxystearate is the only solubilizing agent, for use in the treatment of ocular hypertension, glaucoma or for reducing intraocular pressure.

Another embodiment of the invention relates to an ophthalmic aqueous composition in the form of solution comprising 0.005% to 0.10% w/w hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester, from 0.5% w/w to 1.5% w/w macrogol 15 hydroxystearate wherein macrogol 15 hydroxystearate is the only solubilizing agent, for use in the treatment of ocular hypertension, glaucoma or for reducing intraocular pressure.

Another embodiment of the invention relates to a method of treating ocular hypertension or glaucoma or to a method of reducing intraocular pressure comprising administering to a patient in need thereof a therapeutically effective amount of the above defined ophthalmic aqueous composition in the form of solution.

Another embodiment of the invention relates to a method of treating ocular hypertension or glaucoma or to a method of reducing intraocular pressure comprising administering to a patient in need thereof a therapeutically effective amount of an ophthalmic aqueous composition in the form of solution comprising 0.005% w/w to 0.065% w/w hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester, from 0.5% w/w to 1.5% w/w macrogol 15 hydroxystearate and a pharmaceutically acceptable aqueous vehicle, wherein macrogol 15 hydroxystearate is the only solubilizing agent.

Another embodiment of the invention relates to a method of treating ocular hypertension or glaucoma or to a method of reducing intraocular pressure comprising administering to a patient in need thereof a therapeutically effective amount of an ophthalmic aqueous composition in the form of solution comprising from 0.005% w/w to 0.065% w/w hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester, 1.0% w/w macrogol 15 hydroxystearate, 0.016% w/w benzalkonium chloride, 0.05% w/w ethylenediaminetetraacetic acid disodium salt dihydrate, sodium phosphate dibasic heptahydrate and boric acid and water, wherein the pH of the ophthalmic solution is 6 and wherein macrogol 15 hydroxystearate is the only solubilizing agent; preferably the amount of hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester in the ophthalmic solution is from 0.01% w/w to 0.065% w/w, most preferably is 0.042% w/w, 0.021% w/w or 0.065% w/w; optionally the ophthalmic solution further comprises HCl 1.2M/NaOH 1M to adjust the pH to pH 6.0.

Another embodiment of the invention relates to a method of treating ocular hypertension or glaucoma or to a method of reducing intraocular pressure comprising administering to a patient in need thereof a therapeutically effective amount of an ophthalmic aqueous composition in the form of solution consisting of: from 0.005% w/w to 0.065% w/w hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester, 1.0% w/w macrogol 15 hydroxystearate, 0.016% w/w benzalkonium chloride, 0.05% w/w ethylenediaminetetraacetic acid disodium salt dihydrate, 2.76% w/w sorbitol, 1.33% w/w sodium phosphate dibasic heptahydrate, 0.5% w/w boric acid and water, and having pH 6; preferably in the ophthalmic composition in the form of solution used in above method the amount of hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester is 0.01% w/w to 0.065% w/w, most preferably is 0.042% w/w, 0.021% w/w or 0.065% w/w; optionally the above ophthalmic aqueous composition in the form of solution further include HCl 1.2M/NaOH 1M to adjust the pH to 6.0.

The ophthalmic compositions of the invention may be administered as an eye drop for treating a chronic ophthalmic disease such as glaucoma or ocular hypertension. The ophthalmic solution is intended to be generally administered once per day in each eye, on a daily frequency.

Another embodiment of the invention relates to a process for manufacturing the ophthalmic aqueous solution of the invention, the process comprises the following steps:

Step 1) preparation of a concentrated solution of hexanoic acid, 6-(nitrooxy)-, (1S,2E)-3-[(1R,2R,3S,5R)-2-[(2Z)-7-

(ethylamino)-7-oxo-2-hepten-1-yl]-3,5-dihydroxycyclopentyl]-1-(2-phenylethyl)-2-propen-1-yl ester (API concentrated solution) which comprises:

1a) heating a mixture of water for injection and polyoxyl 15 hydroxystearate at 32° C. until the polyoxyl 15 hydroxystearate is melted;

1b) adding the mixture melted polyoxyl 15 hydroxystearate/water to the pre-weighed hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester (API).

1c) mixing the obtained mixture until full dissolution of hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester while maintaining the mixture at a temperature of 32° C.; the amount of water for injection used in Step 1a) is about the 1.5% of the total weight of water used in the preparation; the amounts of polyoxyl 15 hydroxystearate and of hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester are their total weights corresponding to their percentage in the final solution.

Step 2) Preparation of an aqueous solution of the remaining vehicle ingredients by adding in a manufacturing tank containing water for injection the excipients in the specific following order: edetate disodium dihydrate, the buffer selected from boric acid and sodium phosphate dibasic heptahydrate or citric acid and sodium phosphate dibasic heptahydrate, sorbitol or glycerol and benzalkonium chloride; each excipient being fully dissolved before adding the next excipient and the preparation of the solution is carried out at a temperature from 25° C. to 30° C.; the amount of each excipient is its total weight corresponding to its percentage in the final ophthalmic solution; the water for injection used in Step 2) is about 80% to 90% of the total weight in the final ophthalmic solution.

The above reported order of addition of the excipients must be respected in order to comply with the pH and the tonicity requirements, pH 6.0 and 300 mOsm/kg.

Step 3) Preparation of the bulk ophthalmic solution by adding the API concentrated solution of Step 1 into the manufacturing tank containing the aqueous solution of Step 2 and water for injection up to the targeted final weight.

Optionally the pH of the bulk ophthalmic solution is adjusted to pH 6.0 with sodium hydroxide 1M or hydrochloric acid 1.2M.

Step 4) Sterilization of the bulk ophthalmic solution by filtering the bulk ophthalmic solution of Step 3 through a Polyethersulfone (PES) filters having pore size of about 0.2 μm.

Step 5) Optionally, the bulk ophthalmic solution is filled in low density polyethylene (LDPE) ophthalmic primary containers.

Optionally, when the ophthalmic aqueous solution further includes a viscosity-adjusting agent, in Step 2) the viscosity agent is added in the manufacturing tank containing the water for injection as first component and, once it is fully dissolved, the other excipients are added.

Another embodiment of the invention relates to a process for manufacturing of antimicrobial preservative free ophthalmic aqueous solution of the invention, the process comprises the following steps:

Step 1) preparation of a concentrated solution of hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester (API concentrated solution) which comprises:

1a) heating a mixture of water for injection and polyoxyl 15 hydroxystearate at 32° C. until the polyoxyl 15 hydroxystearate is melted;

1b) adding the mixture melted polyoxyl 15 hydroxystearate/water to the pre-weighed hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester (API).

1c) mixing the obtained mixture until full dissolution of hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester while maintaining the mixture at a temperature of 32° C.; the amount of water for injection used in Step 1a) is about the 1.5% of the total weight of water used in the preparation; the amounts of polyoxyl 15 hydroxystearate and of hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester are their total weights corresponding to their percentage in the final solution.

Step 2) Preparation of an aqueous solution of the remaining vehicle ingredients by adding in a manufacturing tank containing water for injection the excipients in the fic following order: buffer and the tonicity agent; each excipient being fully dissolved before adding the next excipient and the preparation of the solution is carried out at a temperature from 25° C. to 30° C.; the amount of each excipient is its total weight corresponding to its percentage in the final ophthalmic solution; the water for injection used in Step 2) is about 80% to 90% of the total weight in the final ophthalmic solution.

The above reported order of addition of the excipients must be respected in order to comply with the pH and the tonicity requirements, pH 6.0 and 300 mOsm/kg.

Step 3) Preparation of the bulk ophthalmic solution by adding the API concentrated solution of Step 1 into the manufacturing tank containing the aqueous solution of Step 2 and water for injection up to the targeted final weight.

Optionally the pH of the bulk ophthalmic solution is adjusted to pH 6.0 with sodium hydroxide 1M or hydrochloric acid 1.2M.

Step 4) Sterilization of the bulk ophthalmic solution by filtering the bulk ophthalmic solution of Step 3 through a Polyethersulfone (PES) filters having pore size of about 0.2 μm.

Step 5) Optionally, the bulk ophthalmic solution is filled in low density polyethylene (LDPE) ophthalmic primary containers.

When the ophthalmic aqueous solution further includes a viscosity-adjusting agent, in Step 2) the viscosity agent is added in the manufacturing tank containing the water for injection as first component and, once it is fully dissolved, the other excipients are added.

EXAMPLE 1

Preparation of an ophthalmic composition containing hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester (NCX 470) 0.042% w/w (100 liters batch)

The ophthalmic composition ingredients are listed below:

| | |
|---|---|
| NCX 470 = Hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl-1-(2-phenylethyl)-2-propen-1-yl ester (API) | 42.0 g |
| Polyoxyl 15 hydroxystearate (Kolliphor ® HS 15) | 1000 g |
| Benzalkonium Chloride (50% solution) | 32.0 g |
| Edetate disodium dihydrate | 50 g |
| Boric acid | 500 g |
| Sorbitol | 2760 g |
| Sodium phosphate dibasic heptahydrate | 1326 g |
| Water for injection | q.s. to 100 kg |

Step 1) Preparation of API Concentrated Solution 1.5 L of water for injection at about 32° C. was added to 1,000 g of Polyoxyl 15 hydroxystearate pre-weighted in a container which was placed in a hot water bath until polyoxyl 15 hydroxystearate was completely melted. The melted polyoxyl 15-hydrostearate/water mixture was added to a 4 L batch can containing 42 g of NCX-470.

The 4 L batch can was thermostated at 32° C. with a water bath and the API solution was stirred until all ingredients were fully dissolved and maintained under continuous stirring until it was added to the solution of remaining excipients vehicle.

Step 2) Preparation of the Solution of Remaining Excipients Vehicle

100 L of water for injection were poured in a manufacturing tank made of stainless steel (316L grade) and cooled between 25° C. to 30° C. About 12 liters of this water for injection was pulled from the tank and stored in another container for use during the preparation.

The following compounds were added according exactly the following order to the manufacturing tank containing the water under continuous stirring; each compound was fully dissolved before adding the next compound:

50 g of edetate disodium dihydrate;
500 g of boric acid;
1326 g of sodium phosphate dibasic heptahydrate ($Na_2HPO_4 \cdot 7H_2O$);
2760 g of Sorbitol;
32 g of Benzalkonium chloride solution at 50%;
the vessel containing the benzalkonium chloride solution was rinsed multiple times with sufficient water for injection and the rinses were added to the manufacturing tank to complete the transfer.

Step 3) Preparation of the Bulk Ophthalmic Solution

The API concentrated solution was transferred into the manufacturing tank; the 4 L batch can was rinsed with water for injection and the rinses were added to the bulk to complete the transfer.
Water for injection was added to the manufacturing tank to adjust a final targeted weight of 100 kg.

Step 4) Sterilization of the Bulk Ophthalmic Solution

The ophthalmic solution was sterilized by redundant filtration through 0.2 μm Polyethersulfone (PES) filters (Supor®).

Step 5) Bulk Ophthalmic Solution Filling in LDPE Ophthalmic Bottles

After the filtration step, the ophthalmic solution was filled into LDPE multidose containers of appropriate volume under a grade A environment according to conventional aseptic process practices.

EXAMPLE 2

Stability Study

Ophthalmic formulations of the invention stored in multidose Low Density Poly-Ethylene (LDPE) containers sterilized with different sterilization methods were tested for stability The stability of ophthalmic formulations containing NCX 470, 0.042% w/w were evaluated at 25° C., at initial, at 3.5 months and at 6 months, 9 months (long term storage condition) and for accelerated stability at 40° C., at not more than 25% relative humidity (RH), at initial, at 3.5 months and at 6 months.

Ophthalmic Formulations Composition:

| | |
|---|---|
| NCX 470 (API) | 0.042 g |
| Benzalkonium Chloride (50% solution) | 0.032 g |
| Polyoxyl 15 hydroxystearate | 1.00 g |
| Edetate disodium dihydrate | 0.05 g |
| Boric acid | 0.50 g |
| Sorbitol | 2.76 g |
| Sodium phosphate dibasic heptahydrate | 1.326 g |
| Sodium hydroxide and Hydrochloric acid | q.s. to adjust to pH 6.0 |
| Water for injection | q.s. to 100 g |
| Results are shown in Tables 1 to 4 | |

The results of the stability tests at 25° C. (Table 1 and 3) and 40° C. (Table 2 and 4) demonstrated good stability of the ophthalmic solutions according to the invention, so that the ophthalmic solutions filled in a LDPE primary containers are expected to have a product shelf-life of at least 24 month in storage conditions at ambient temperature.

EXAMPLE 2A

Primary container: Transparent LDPE/Pre-sterilized by radiation (gamma rays/25 kGy)
Primary container configuration: 2.5 mL fill in a 7.5 mL bottle.

TABLE 1

| Storage Condition: 25° C./40% RH | | Time (Months) | |
|---|---|---|---|
| Test | Acceptance Criteria | Initial | 3.5 Months | 6 Months |
| Appearance | Clear, colorless to slightly yellow solution, free from visible particulates | Complies | Complies | Complies |
| pH | 5.5-6.5 | 6.0 | 5.9 | 6.1 |
| Osmolality (mOsm/kg) | 280-340 | 301 | 307 | 306 |
| NCX470 content | 90%-110% of the target | 100.0% | 100.5% | 102.1% |

TABLE 2

| Storage Condition: 40° C./<25% RH | | Time (Months) | | |
| --- | --- | --- | --- | --- |
| Test | Acceptance Criteria | Initial | 3.5 Months | 6 Months |
| Appearance | Clear, colorless to slightly yellow solution, free from visible particulates | Complies | Complies | Complies |
| pH | 5.5-6.5 | 6.0 | 5.9 | 6.0 |
| Osmolality (mOsm/kg) | 280-340 | 301 | 321 | 330 |
| NCX 470 content | 90%-110% of the target | 100.0% | 97.6% | 97.9% |

EXAMPLE 2B

Primary container: LDPE/Pre-sterilized by Ethylene Oxide
Primary container configuration: 2.5 mL fill in a 7.5 mL bottle

TABLE 3

| Storage Condition: 25° C./uncontrolled RH | | Time: (Months) | | | | |
| --- | --- | --- | --- | --- | --- | --- |
| Test | Acceptance Criteria | Initial | 2 Months | 3 Months | 6 Months | 9 Months |
| Appearance | Clear, colorless to slightly yellow solution, free from visible particulates | Complies | Complies | Complies | Complies | Complies |
| pH | 5.5-6.5 | 6.0 | 5.9 | 5.9 | 5.9 | 6.0 |
| Osmolality (mOsm/kg) | 280-340 | 308 | 306 | 307 | 302 | 302 |
| NCX 470 content | 90%-110% of the target | 100.5% | 99.5% | 100.2% | 99.3% | 101.4% |

TABLE 4

| Storage Condition: 40° C./<25% RH | | Time (Months) | | | | |
| --- | --- | --- | --- | --- | --- | --- |
| Test | Acceptance Criteria | Initial | 1 Month | 2 Months | 3 Months | 6 Months |
| Appearance | Clear, colorless to slightly yellow solution, free from visible particulates | Complies | Complies | Complies | Complies | Complies |
| pH | 5.5-6.5 | 6.0 | 5.9 | 5.9 | 5.9 | 5.9 |
| Osmolality (mOsm/kg) | 280-340 | 308 | 307 | 307 | 313 | 324 |
| NCX 470 content | 90%-110% of the target | 100.5% | 101.2% | 100.0% | 99.5% | 97.6% |

As a conclusion, the ophthalmic solution from the present invention can be packaged in LDPE primary containers, whatever is the pre-sterilization mode of such containers. Multidose primary containers can be sterilized either by gamma radiation or ethylene oxide gas. Single-use or unit dose containers produced by BFS® (blow-fill-seal) technology provides native LDPE containers, naturally sterile, and such LDPE material preparation is appropriate for packaging the preservative free ophthalmic solution from the present invention too.

EXAMPLE 3

Antimicrobial Effectiveness Tests

EXAMPLE 3A

Antimicrobial effectiveness tests were performed to assess the ability of the ophthalmic solutions according to the present invention to meet the antimicrobial preservative efficacy criteria.

Ophthalmic solutions containing Edetate disodium 0.05% (w/w) (see Table 5) and different concentrations of benzalkonium chloride (see Table 6) were tested. The ophthalmic compositions were prepared by applying the process disclosed in Example 1.

The tests were performed according to the procedure for the performance of the test disclosed in United States Pharmacopoeia, Monograph <51>, "Antimicrobial Effectiveness Testing" (AET). The success of this USP test is equivalent of matching the European Pharmacopoeia criteria B.

The results reported in Table 6 showed that the ophthalmic compositions containing benzalkonium chloride in a range from 0.012% (w/w) to 0.02% (w/w) met the criteria for microbial effectiveness and passed the Antimicrobial Effectiveness Testing (AET).

NCX 470=Hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester

TABLE 5

Ophthalmic solutions

| Compound | Amount |
| --- | --- |
| NCX 470 | 0.042 g |
| Polyoxyl 15 hydroxystearate | 1.00 g |
| Edetate disodium dihydrate | 0.05 g |
| Boric acid | 0.50 g |
| Sorbitol | 2.76 g |
| Sodium phosphate dibasic heptahydrate | 1.326 g |
| Sodium hydroxide and Hydrochloric acid | q.s. to adjust to pH 6.0 |
| Water for injection | q.s. to 100 g |

TABLE 6

BAK concentrations and AET results (USP <51>)

| BAK (% w/w) | 0.02 | 0.018 | 0.016 | 0.014 | 0.012 | 0.010 |
| --- | --- | --- | --- | --- | --- | --- |
| AET criteria | Passes | Passes | Passes | Passes | Passes | Fails |

EXAMPLE 3B

To assess the effect of EDTA as antimicrobial preservative aid, the efficacy to meet the preservative criteria of an ophthalmic composition containing benzalkonium chloride (0.016 w/w) and Edetate disodium (0.05% w/w)(Formulation A—Table 7) and of an ophthalmic composition containing benzalkonium chloride (0.016% w/w) but not Edetate disodium (Formulation B—Table 7) were assessed.

The results showed that the presence of Edetate disodium is required to meet the preservative criteria defined in the US Pharmacopoeia monograph <51> or European Pharmacopoeia criteria B.

TABLE 7

Ophthalmic solutions and AET results

| Composition | Formulation A | Formulation B |
| --- | --- | --- |
| NCX 470 (API) | 0.042 g | 0.042 g |
| Benzalkonium chloride | 0.016 g | 0.016 g |
| Polyoxyl 15 hydroxystearate | 1.00 g | 1.00 g |
| Edetate disodium dihydrate | 0.05 g | 0 g |
| Boric acid | 0.50 g | 0.50 g |
| Sorbitol | 2.76 g | 2.76 g |
| Sodium phosphate dibasic heptahydrate | 1.326 g | 1.326 g |
| Sodium hydroxide and/or Hydrochloric acid | Adjust to pH 6.0 | Adjust to pH 6.0 |
| Water for injection | q.s. to 100 g | q.s. to 100 g |
| AET results (USP<51>) | Passes | Fails |

WO 2013/003827 (Allergan) discloses that polyoxyl 15 hydroxystearate improves antimicrobial preservative effectiveness allowing reducing the dose of the antimicrobial preservative agent benzalkonium chloride for matching USP <51> or EP-criteria B. The preservative studies carried out with the ophthalmic solutions of the invention showed that polyoxyl 15 hydroxystearate does not improve the antimicrobial preservative efficacy of benzalkonium chloride and that for ensuring antimicrobial preservation efficacy of the ophthalmic solutions must contain an amount of benzalkonium chloride that must be higher than 0.12% w/w in the presence of EDTA. 0.5% w/w. The most appropriate antimicrobial preservative dose target was achieved with a mixture of 0.16% w/w benzalkonium chloride and 0.05% w/w EDTA.

EXAMPLE 4

Pharmacokinetic Evaluation in Dutch Belted Rabbits after Single Ocular Instillation Study 1

Hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester is a dual-acting prostaglandin analog derivative that combines the pharmacological activity of bimatoprost with nitric oxide. Bimatoprost free acid is one of the active metabolites of Hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester; in this study bimatoprost free acid level was used as marker to compare the ocular penetration of hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester after topical instillation of an aqueous ophthalmic solution of the invention with respect to a commercially available eyedrop containing bimatoprost and a reference formulation containing hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester.

The objective of this study was to comparatively assess the amounts of bimatoprost free acid in aqueous humor samples taken following instillation of the tested aqueous ophthalmic solutions.

Two different aqueous ophthalmic solutions containing hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester (Formulations 1 and 2) and a commercially available eyedrop containing bimatoprost (Formulation 3) were evaluated in a rabbit ocular pharmacokinetic study.

The two different aqueous solutions comprising hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester are an ophthalmic solution according to the invention (Formulation 1), and the formulation disclosed in WO 2009/136281 (Formulation 2).

Tested Solutions

Table 8 reports the vehicles of the two aqueous ophthalmic solutions containing hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester 0.042% w/w.

TABLE 8

Vehicle composition of Formulations 1 and 2

| Components (% w/w) | Formulation 1 | Formulation 2 |
|---|---|---|
| Macrogol 15-hydroxystearate | 1.0 | — |
| Polysorbate 80 | — | 1.0 |
| Benzalkonium chloride | 0.02 | 0.02 |
| Boric acid | 0.5 | 0.5 |
| Disodium Edetate dihydrate | 0.05 | 0.05 |
| Sorbitol | 2.9 | 2.9 |
| Sodium phosphate dibasic heptahydrate (Na2HPO4 7H2O) | 1.43 | 1.43 |
| Sodium hydroxide and/or hydrochloric acid | q.s. to pH 6.0 | q.s. to pH 6.0 |
| Water for injection | q.s. to 100 g | q.s. to 100 g |

Formulation 3 (Commercially Available Eyedrop/Lumigan®, Allergan)

Active principle: Bimatoprost 0.03%;

The concentration 0.042% w/w of hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester is equimolar with respect to the moles of bimatoprost of the commercially available eyedrop (Formulation 3).

Material

Macrogol 15-hydroxystearate is the commercially available Kolliphor® HS15 (BASF). Polysorbate 80 is the commercially available Polysorbate 80 Super Refined® (Croda).

Experimental Procedure

Groups of 10 male naïve Dutch Belted Rabbits were assigned to the study and administered either with Formulations 1 and 2 or Formulation 3 by instillation to each eye at nominal target doses of 12.6 μg/eye for Formulations 1 and 2 and 9 g/eye for bimatoprost solution. An additional group of 5 males was employed to provide blank control matrix (aqueous humor) for bio-analytical purposes. During the study, body weight measurements and clinical observations were performed and at pre-determined time points, animals were sacrificed for the purposes of aqueous humor (AH) harvesting at 1 h, 2 h, 4 h and 8 h.

No clinical signs associated with dosing where observed during the study.

Results

The results reported in Table 9 showed that the aqueous ophthalmic solution according to the invention (Formulation 1), demonstrated greater exposure to bimatoprost acid (in terms of $C_{max}$ and AUC values) compared with that achieved following administration of the reference formulation (Formulation 2) and the commercially available eyedrop (Formulation 3).

$C_{max}$ is the maximum concentration that bimatoprost free acid achieved in the aqueous humor. AUC (area under the curve) represents the total amount of bimatoprost free acid in the aqueous humor over time that is available to produce a biological effect.

TABLE 9

Mean pharmacokinetic parameters derived from the aqueous humor levels of bimatoprost free acid

| | Formulation 1 | Formulation 2 | Formulation 3 |
|---|---|---|---|
| Cmax (ng/mL) | 83.9 | 55.3 | 30.3 |
| AUCt (ng · h/mL) | 259 | 197 | 73.2 |

Study 2

The aim of this study was to assess the aqueous humor content of bimatoprost free acid following topical ocular dosing with three different aqueous ophthalmic solutions containing hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester (0.042% w/w) in three different vehicles reported in Table 10.

Vehicle 1 and 2 contain polysorbate 80 that is the solubilizer agent of the formulation disclosed in the prior art document WO2009/136281; vehicle 1 differs from vehicle 2 in that it contains benzalkonium chloride whereas vehicle 2 does not contains benzalkonium chloride.

Vehicle 3 contains a mixture of polysorbate 80 and macrogol 15-hydroxystearate.

Tested Solutions

Table 10 reports the vehicles of the aqueous ophthalmic solutions containing hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester 0.042% w/w.

An additional reference formulation was tested; this formulation is the commercially available eyedrop containing active bimatoprost 0.03%.

TABLE 10

Vehicles composition

| Components (% w/w) | Vehicle 1 | Vehicle 2 | Vehicle 3 |
|---|---|---|---|
| Polysorbate 80 | 1.0 | 1.0 | 0.5 |
| Macrogol 15-hydroxystearate | — | — | 0.5 |
| Benzalkonium chloride | 0.02 | — | 0.02 |
| Glycerol | 0.69 | 0.69 | 0.69 |
| Citric acid monohydrate | 0.34 | 0.34 | 0.34 |
| Sodium phosphate dibasic heptahydrate (Na2HPO4 7H2O) | 2.26 | 2.26 | 2.26 |
| Water for injection | q.s. to 100 g | q.s. to 100 g | q.s. to 100 g |
| pH | 6.7 | 6.7 | 6.7 |

Material

Macrogol 15-hydroxystearate is the commercially available Kolliphor® HS15 (BASF). Polysorbate 80 is the commercially available Polysorbate 80 Super Refined® (Croda).

Experimental Procedure

Forty animals were included in the study. They were allocated into four groups of 10 animals/group and were administered with the above reported tested aqueous ophthalmic solutions All animals included in the study were administered by ocular instillation of both eyes by means of a graduated pipette at a volume of 30 L/eye. Two animals per formula were sacrificed at 0 h (pre-dose), 1 h, 2 h, 4 h and 8 h, and aqueous humor samples were obtained immediately from both eyes.

Results

The pharmacokinetic data reported in Table 11 showed that the exposure to bimatoprost acid (in terms of $C_{max}$ and AUC values) of the aqueous ophthalmic solutions containing Vehicle 1 or Vehicle 2 are equivalent whereas the aqueous ophthalmic solution containing Vehicle 3 showed a greater exposure (higher concentration of bimatoprost free acid in the aqueous humor) to bimatoprost free acid.

The lowest exposure parameters for bimatoprost acid were obtained in group of the Reference formulation.

Moreover the results demonstrated that benzalkonium chloride did not exert any effect on the ocular penetration of hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester hexanoate up to a 0.02% w/w concentration, indeed the pharmacokinetic data are considered equivalent for the two aqueous ophthalmic solutions containing Vehicles 1 or 2.

TABLE 11

Mean pharmacokinetic parameters derived from the aqueous humor levels of bimatoprost free acid

|  | Vehicle 1 | Vehicle 2 | Vehicle 3 | Ref. formulation |
|---|---|---|---|---|
| Cmax (ng/mL) | 43.97 | 45.29 | 111.49 | 28.45 |
| AUCt (ng · h/mL) | 202 | 185 | 373 | 77.4 |

In conclusion, the results of the above reported studies demonstrated that macrogol 15-hydroxystearate is able to enhance the ocular penetration of hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester. The enhanced absorption is a surprising effect because it does not depend on the known solubilizing activity of macrogol 15-hydroxystearate since in all the tested aqueous ophthalmic solutions the therapeutic active compound was solubilized.

Indeed the solubility of hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester in aqueous solutions at pH 6.0 containing 0.5% (w/w) of macrogol 15-hydroxystearate (Kolliphor® HS15) or 0.5% (w/w) polysorbate 80 (Tween® 80) are 0.070% (w/w) and 0.074% (w/w) respectively, and so considered basically equivalent, therefore in all the tested vehicles hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester was solubilized.

Moreover, the results of Study 2 showed that benzalkonium chloride did not have effect on the ocular bioavailability of the active compound; indeed vehicle 1, which contains polysorbate 80 and benzalkonium chloride, and vehicle 2, which contains polysorbate 80 but not benzalkonium chloride, showed equivalent concentration of bimatoprost free acid in the aqueous humor.

EXAMPLE 5

Intraocular Pressure in Ocular Normotensive Beagle Dogs

In this study the efficacies in lowering intraocular pressure (IOP) in ocular normotensive Beagle dogs of an ophthalmic aqueous composition according to the present invention were assessed.

Tested Compositions

Formulation 1

Formulation 1 Contains 0.042% w/w of hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester;
Macrogol 15-hydroxystearate: 1.0% w/w
Benzalkonium chloride: 0.016% w/w
Boric acid: 0.5% w/w
Disodium Edetate: 0.05% w/w
Sorbitol: 2.76% w/w
Sodium phosphate dibasic heptahydrate ($Na_2HPO_4$ $7H_2O$): 1.326% w/w
Water for injection q.s. to 100 g
Compositions have a final pH of 6.0 and an osmolality of about 300 mOsm/kg Experimental Procedure The tested aqueous compositions were administered by topical route to the conjunctival sac of both eyes of Beagle dogs twice a day, at approximately 4-hour intervals, for 28 days. Two groups, each containing three males and three female of Beagle dogs, were included:
Group 1 (Control animals): vehicle
Group 2: Formulation 1
Each animal received 30 µL/eye of the indicated substances on each treatment.

The first dose of the day was administered between 7 and 9 am, every day approximately at the same time.

The test item was placed by means of an automatic pipette in the conjunctiva of both eyes of each animal after gently pulling the lower lid away from the eyeball. The lids were then gently held together for about one second to prevent loss of test item.

Intraocular pressure was measured by an electronic tonometer, before the administration and at 1-1.5 hours after the daily dose on treatment day 2, 4, 8, 20 and 27.

Pupils were instilled with oxybuprocaine hydrochloride (Prescaina® 0.4%) or oxybuprocaine hydrochloride, tetracaine hydrochloride (Colircusi Doble® Anestesico) eye drops before measuring the intraocular pressure.

Results

The results are reported in Table 12 as IOP change versus baseline.

The aqueous compositions of the invention were effective in lowering IOP in ocular normotensive dogs. Furthermore, repeated daily dosing of the aqueous compositions of the invention resulted in sustained IOP lowering activity over time.

TABLE 12

IOP-Lowering Activity in Ocular Normotensive Dogs;
Intraocular pressure change versus baseline

|  | Day 2 (mmHg) | Day 4 (mmHg) | Day 8 (mmHg) | Day 20 (mmHg) | Day 27 (mmHg) |
|---|---|---|---|---|---|
| Formulation 1 (0.042%) | −9.2 ± 1.5 | −7.5 ± 1.1 | −9.0 ± 1.3 | −7.9 ± 1.3 | −8.2 ± 1.2 |
| Vehicle | −2.5 ± 0.6 | −2.7 ± 0.9 | −1.6 ± 0.6 | −3.2 ± 0.6 | −1.8 ± 0.6 |

EXAMPLE 6

Stability Study

The stability of an ophthalmic formulation of the invention containing 0.065% w/w NCX 470 stored in 7.5 mL Gamma-rays sterilized LDPE bottles was evaluated at 25° C., at initial, at 3 months and at 6 months and for accelerated stability at 40° C., at not more than 25% relative humidity (RH), at initial, at 3 months and at 6 months.
The ophthalmic formulation was prepared according to method described in Example 1.

Ophthalmic Formulation Composition 0.065% w/w hexanoic acid, 6-(nitrooxy)-, (1S,2E)-3-[(1R,2R,3S,5R)-2-[(2Z)-7-(ethyl amino)-7-oxo-2-hepten-1-yl]-3,5-dihydroxycyclopentyl]-1-(2-phenylethyl)-2-propen-1-yl ester (NCX470);
1.0% w/w macrogol 15 hydroxystearate;
0.016% w/w benzalkonium chloride;
0.05% w/w ethylenediaminetetraacetic acid disodium salt dehydrate;
2.76% w/w sorbitol;
1.326% % w/w sodium phosphate dibasic heptahydrate;
0.5% w/w boric acid; and
Water for injection q.s. to 100% w/w;
Primary container configuration: 2.5 mL fill in a 7.5 mL bottle.

TABLE 13

| Storage Condition: 25° C./40% RH | | Time (Months) | | |
|---|---|---|---|---|
| Test | Acceptance Criteria | Initial | 3 Months | 6 Months |
| Appearance | Clear, colorless to slightly yellow solution, free from visible particulates | Complies | Complies | Complies |
| pH | 5.5-6.5 | 6.0 | 6.0 | 6.0 |
| Osmolality (mOsm/kg) | 280-340 | 297 | 302 | 301 |
| NCX470 content | 90%-110% of the target | 97.3 | 97.0 | 98.0 |

TABLE 14

| Storage Condition: 40° C./<25% RH | | Time (Months) | | |
|---|---|---|---|---|
| Test | Acceptance Criteria | Initial | 3 Months | 6 Months |
| Appearance | Clear, colorless to slightly yellow solution, free from visible particulates | Complies | Complies | Complies |
| pH | 5.5-6.5 | 6.0 | 6.0 | 6.0 |
| Osmolality (mOsm/kg) | 280-340 | 297 | 308 | 324 |

TABLE 14-continued

| Storage Condition: 40° C./<25% RH | | Time (Months) | | |
|---|---|---|---|---|
| Test | Acceptance Criteria | Initial | 3 Months | 6 Months |
| NCX 470 content | 90%-110% of the target | 97.3 | 98.4 | 105.0 |

The results of the stability tests at 25° C. (Table 13) and at 40° C. (Table 14) demonstrated that the ophthalmic formulations according to the invention were stable, so that the ophthalmic solutions are expected to have a product shelf-life of at least 24 months in storage conditions at ambient temperature when stored LDPE containers.

EXAMPLE 7

Preparation of an ophthalmic preservative free composition containing 0.065% w/w hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester (NCX470).
The ophthalmic composition ingredients are listed below:

| | |
|---|---|
| NCX 470 | 65 g |
| Polyoxyl 15 hydroxystearate (Kolliphor ® HS15): | 1000 g |
| Boric acid: | 500 g |
| Sorbitol: | 2760 g |
| Dibasic sodium phosphate, heptahydrate: | 1300 g |
| Sodium Hydroxide and/or hydrochloric acid: q.s. to adjust to pH | 6.0 |
| Water for injection: | q.s. to 100 Kg |

Step 1) Preparation of API Concentrated Solution 1.5 L of water for injection at about 32° C. was added to 1000 g of Polyoxyl 15 hydroxystearate pre-weighted in a container which was placed in a hot water bath until polyoxyl 15 hydroxystearate was completely melted. The melted polyoxyl 15-hydrostearate/water mixture was added to a 4 L batch can containing 65 g of NCX-470.
The 4 L batch can was thermostated at 32° C. with a water bath and the API solution was stirred until all ingredients were fully dissolved and maintained under continuous stirring until it was added to the solution of remaining excipients vehicle.

Step 2) Preparation of the Solution of Remaining Excipients Vehicle

100 L of water for injection were poured in a manufacturing tank made of stainless steel (316L grade) and cooled between 25° C. to 30° C. About 12 liters of this water for injection was pulled from the tank and stored in another container for use during the preparation.
The following compounds were added according to the following order to the manufacturing tank containing the water under continuous stirring; each compound was fully dissolved before adding the next compound:
500 g of boric acid;
1300 g of sodium phosphate dibasic heptahydrate ($Na_2HPO_4$ $7H_2O$);
2760 g of Sorbitol;
The vessel containing the solution was rinsed multiple times with sufficient water for injection and the rinses were added to the manufacturing tank to complete the transfer.

Step 3) Preparation of the bulk ophthalmic solution

The API concentrated solution was transferred into the manufacturing tank; the 4 L batch can was rinsed multiple times with water for injection and the rinses were added to the bulk to complete the transfer.

Water for injection was added to the manufacturing tank to adjust a final targeted weight of 100 kg.

pH can be fine-tuned more precisely by using sodium hydroxide and/or hydrochloric acid.

Step 4) Sterilization of the Bulk Ophthalmic Solution

The ophthalmic solution was sterilized by redundant filtration through 0.2 μm Polyethersulfone (PES) filters (Supor® from Pall).

Step 5) Bulk Ophthalmic Solution Filling in LDPE Ophthalmic Primary Containers After the filtration step, the ophthalmic solution was filled into a LDPE preservative free multidose primary container system (e.g. Aptar OSD® system) of appropriate volume under a grade A environment according to conventional aseptic process practices. As another preservative free primary container system option, the bulk sterile solution can be filled into single-dose primary containers, for example single-dose primary containers produced by BFS technology (Blow-Fill-Seal®/Rommelag).

EXAMPLE 8

Stability Study

The stability of preservative free ophthalmic formulations of the invention containing 0.01% w/w NCX 470 and 0.18% NCX 470 stored in 5 mL glass bottles was evaluated at 25° C. and at 40° C., at different time points.

The ophthalmic formulations were prepared according to method described in Example 7. In these formulations the buffer system is mixture of sodium phosphate dibasic heptahydrate and citric acid monohydrate and the tonicity agent is glycerol.

0.01% w/w NCX 470 Ophthalmic Formulation Composition 0.01% w/w hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester (NCX470);
1.5% w/w macrogol 15 hydroxystearate (Kolliphor® HS15);
0.52% w/w glycerol;
2.33% w/w sodium phosphate dibasic heptahydrate;
0.36% w/w citric acid monohydrate; and
water for injection q.s. to 100% w/w.
Primary container configuration: 3 mL fill in a 5 mL glass bottle.

0.18% w/w NCX 470 Ophthalmic Formulation Composition:
0.18% w/w hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl) 2-propen-1-yl ester (NCX470);
1.5% w/w macrogol 15 hydroxystearate (Kolliphor® HS15);
0.52% w/w glycerol;
2.33% w/w sodium phosphate dibasic heptahydrate;
0.36% w/w citric acid monohydrate; and
water for injection q.s. to 100% w/w.

Primary container configuration: 3 mL fill in a 5 mL bottle.

The stability results of the two ophthalmic formulations are reported in the below tables 15-18; the results showed that the preservative free ophthalmic formulations of the invention were stable.

TABLE 15

Stability data of 0.01% w/w NCX 470 ophthalmic formulation

Storage Condition: 25° C./40% RH

| | | | Time (Months) | |
|---|---|---|---|---|
| Test | Acceptance Criteria | Initial | 1.5 Months | 3 Months |
| Appearance | Clear, colorless to slightly yellow solution, free from visible particulates | Complies | Complies | Complies |
| pH | 6.0-7.2 | 6.6 | 6.7 | 6.7 |
| Osmolality (mOsm/kg) | 280-320 | 304 | 310 | 305 |
| NCX470 content | 90%-110% of the target | 100.0 | 100.0 | 100.0 |

TABLE 16

Stability data of 0.01% w/w NCX 470 ophthalmic formulation

Storage Condition: 40° C./<25% RH

| | | | Time (Months) | |
|---|---|---|---|---|
| Test | Acceptance Criteria | Initial | 1.5 Months | 3 Months |
| Appearance | Clear, colorless to slightly yellow solution, free from visible particulates | Complies | Complies | Complies |
| pH | 6.0-7.2 | 6.6 | 6.7 | 6.7 |
| Osmolality (mOsm/kg) | 280-320 | 304 | 312 | 312 |
| NCX 470 content | 90%-110% of the target | 100.0 | 100.0 | 100.0 |

TABLE 17

Stability data of 0.18% w/w NCX 470 ophthalmic formulation

Storage Condition: 25° C./40% RH

| | | | Time (Months) | |
|---|---|---|---|---|
| Test | Acceptance Criteria | Initial | 1.5 Months | 3 Months |
| Appearance | Clear, colorless to slightly yellow solution, free from visible particulates | Complies | Complies | Complies |
| pH | 6.0-7.2 | 6.6 | 6.7 | 6.7 |
| Osmolality (mOsm/kg) | 280-320 | 303 | 310 | 308 |
| NCX470 content | 90%-110% of the target | 102.8 | 101.7 | 100.0 |

EXAMPLE 9 (VISCOUS SOLUTION)

TABLE 18

Stability data of 0.18% w/w NCX 470 ophthalmic formulation

Storage Condition: 40° C./<25% RH

| Test | Acceptance Criteria | Initial | 1.5 Months | 3 Months |
|---|---|---|---|---|
| Appearance | Clear, colorless to slightly yellow solution, free from visible particulates | Complies | Complies | Complies |
| pH | 6.0-7.2 | 6.6 | 6.7 | 6.7 |
| Osmolality (mOsm/kg) | 280-320 | 303 | 314 | 316 |
| NCX 470 content | 90%-110% of the target | 102.8 | 98.9 | 97.2 |

Preparation of an ophthalmic composition containing hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester (NCX 470) 0.065% w/w and a viscosity-adjusting agent.

The ophthalmic composition ingredients are listed below:

| | |
|---|---|
| NCX 470 = Hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester (API) | 65 g |
| Polyoxyl 15 hydroxystearate (Kolliphor ® HS 15) | 1000 g |
| Benzalkonium Chloride (50% solution) | 32 g |
| Edetate disodium dihydrate | 50 g |
| Boric acid | 500 g |
| Sorbitol | 2760 g |
| Sodium phosphate dibasic heptahydrate | 1326 g |
| Hydroxypropyl methylcellulose (HPMC) | 200 g |
| Water for injection | q.s. to 100 kg |

Step 1) Preparation of API Concentrated Solution 1.5 L of water for injection at about 32° C. was added to 1000 g of Polyoxyl 15 hydroxystearate pre-weighted in a container which was placed in a hot water bath until polyoxyl 15 hydroxystearate was completely melted. The melted polyoxyl 15-hydrostearate/water mixture was added to a 4 L batch can containing 65 g of NCX-470. The 4 L batch can was thermostated at 32° C. with a water bath and the API solution was stirred until all ingredients were fully dissolved and maintained under continuous stirring until it was added to the solution of remaining excipients vehicle.

Step 2) Preparation of the Solution of Remaining Excipients Vehicle (Example of Viscous Solutions)

100 L of water for injection were poured in a manufacturing tank made of stainless steel (316L grade) at a temperature higher than 85° C. About 12 liters of this water for injection was pulled from the tank and stored in another container for use during the preparation.

200 g of HPMC (Metolose®/Shin-Etsu) are introduced slowly inside the tank while mixing. The cellulose is introduced slowly over 15 min. Once the polymer has been fully dispersed into the tank, to keep mixing for additional 15 min at a temperature of at least 85° C. After that holding time, to cool the bulk solution down to 25° C.-30° C. temperature.

Then, the following compounds were added according exactly the following order to the manufacturing tank containing the water under continuous stirring; each compound was fully dissolved before adding the next compound:

50 g of edetate disodium dihydrate;
500 g of boric acid;
1326 g of sodium phosphate dibasic heptahydrate ($Na_2HPO_4$ $7H_2O$);
2760 g of Sorbitol;
32 g of Benzalkonium chloride solution at 50%;
the vessel containing the benzalkonium chloride solution was rinsed multiple times with sufficient water for injection and the rinses were added to the manufacturing tank to complete the transfer.

Step 3) Preparation of the Bulk Ophthalmic Solution

The API concentrated solution was transferred into the manufacturing tank; the 4 L batch can was rinsed with water for injection and the rinses were added to the bulk to complete the transfer.

Water for injection was added to the manufacturing tank to adjust the final targeted weight of 100 kg.

Step 4) Sterilization of the Bulk Ophthalmic Solution The ophthalmic solution was sterilized by redundant filtration through 0.2 μm Polyethersulfone (PES) filters (Supor® Pall);

Step 5) Optionally, the bulk ophthalmic solution is filled in low density polyethylene (LDPE) ophthalmic primary containers. Usually, the formulation can be packaged in a multidose ophthalmic bottle with cap and dropper tip enabling to deliver calibrated drops with a controlled drop size. Example of such primary containers can be Rispharm® bottles from Berry-Plastics, Boston Round® from Amcor, 3 pieces bottles from either Gerresheimer, Philips-Medisize, Bormioli or equivalent.

The invention claimed is:

1. An ophthalmic aqueous composition in the form of solution comprising:
   0.005% to 0.10% w/w hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester,
   from 0.5% w/w to 1.5% w/w macrogol 15 hydroxystearate,
   sodium phosphate dibasic heptahydrate,
   boric acid,
   a tonicity agent, and
   water,
   wherein a pH of the composition is 6, and
   wherein macrogol 15 hroxystearate is the only solubilizing agent.

2. An ophthalmic aqueous composition according to claim 1 comprising 0.005% to 0.065% w/w hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester.

3. The ophthalmic aqueous composition according to claim 1 wherein the amount of hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester is 0.021% w/w, 0.042% w/w, 0.065% w/w or 0.10% w/w.

4. The ophthalmic aqueous composition according to claim 1 which comprises 0.013% w/w to 0.02% w/w benzalkonium chloride, 0.03% w/w to 0.07% w/w of an edetate salt.

5. The ophthalmic aqueous composition according to claim 4 wherein the amount of benzalkonium chloride is from 0.013% w/w to 0.02% w/w and the amount of the edetate salt is 0.05% w/w.

6. The ophthalmic aqueous composition according to claim 5 wherein the amount of benzalkonium chloride is 0.016% and the amount of the edetate salt is 0.05% w/w.

7. The ophthalmic aqueous composition according to claim 1 further comprises a pH-adjusting agent.

8. The ophthalmic aqueous composition according to claim 1 wherein the tonicity agent is sorbitol or glycerol.

9. The ophthalmic aqueous composition according to claim 1, comprising:
  1.0% w/w of macrogol 15 hydroxystearate,
  0.016% w/w benzalkonium chloride,
  0.05% w/w ethylenediaminetetraacetic acid disodium salt dihydrate,
  2.76% w/w sorbitol,
  1.33% w/w sodium phosphate dibasic heptahydrate, and
  0.5% w/w boric acid.

10. The ophthalmic aqueous composition according to claim 9 wherein the amount of hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester is 0.021% w/w, 0.042% w/w, 0.065% w/w or 0.10% w/w.

11. An ophthalmic aqueous composition comprising:
  0.10% w/w hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl,
  1.5% w/w macrogol 15 hydroxystearate,
  0.016% w/w benzalkonium chloride,
  0.05% w/w ethylenediaminetetraacetic acid disodium salt dihydrate,
  0.52% w/w glycerol,
  2.33% w/w sodium phosphate dibasic heptahydrate,
  0.36% w/w citric acid monohydrate, and
  water.

12. The ophthalmic aqueous composition according to claim 9 further comprising a pH-adjusting agent selected from hydrochloric acid or sodium hydroxide.

13. The ophthalmic aqueous composition according to claim 9 further comprising a viscosity-adjusting agent.

14. The ophthalmic aqueous composition according to claim 1 further comprising a viscosity-adjusting agent, wherein the viscosity-adjusting agent, is hydroxypropylmethyl cellulose at a concentration less than 0.5% w/w.

15. A method of treatment comprising administering the opthalmic aqueous composition according to claim 1 to a subject in need thereof, wherein the subject suffers from ocualr hypertension or glaucoma.

16. A process for manufacturing the ophthalmic aqueous composition according to claim 8, comprising:
  Step 1) Preparation of a concentrated solution of hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester by:
    1a) heating a mixture of water for injection and polyoxyl 15 hydroxystearate at 32° C. until the polyoxyl 15 hydroxystearate is melted;
    1b) adding the melted polyoxyl 15 hydroxystearate/water mixture to the hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester to provide a mixture, wherein the hexanoic acid, 6-(nitrooxy)-(1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester is pre-weighed;
    1c) mixing the obtained mixture of 1b) until full dissolution of hexanoic acid, 6-(nitrooxy)-(1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester while maintaining the mixture at a temperature of 32° C.; wherein the amounts of polyoxyl 15 hydroxystearate and of hexanoic acid, 6-(nitrooxy)-, (1S,2E)-3-[(1R,2R,3S,5R)-2-[(2Z)-7-(ethylamino)-7-oxo-2-hepten-1-yl]-3,5-dihydroxycyclopentyl]-1-(2-phenylethyl)-2-propen-1-yl ester correspond to their amounts in the final formulation and the amount of water for injection used in Step 1a) is about the 1.5% of the total weight of water used in the process;
  Step 2) Preparation of an aqueous solution of vehicle ingredients by adding excipients to a manufacturing tank containing water for injection, wherein the excipients comprise edetate disodium dihydrate, the buffer comprising a combination of boric acid and sodium phosphate dibasic heptahydrate, or a combination of citric acid and sodium phosphate dibasic heptahydrate, sorbitol or glycerol and benzalkonium chloride, wherein each excipient are added in order as listed, wherein each excipient is fully dissolved before adding the next excipient, and wherein the preparation of the aqueous solution is carried out at a temperature from 25° C. to 30° C.;
  Step 3) Preparation of a bulk ophthalmic solution by adding the solution of Step 1 into the manufacturing tank containing the aqueous solution of Step 2 and water for injection until a targeted final weight is obtained;
  Step 4) Sterilization of the bulk ophthalmic solution by filtering the bulk ophthalmic solution of Step 3 through a Polyethersulfone (PES) filters having pore size of about 0.2 μm.

17. The process according to claim 16 wherein in Step 3) the pH of the bulk ophthalmic solution is adjusted to pH 6.0 with sodium hydroxide or hydrochloric acid.

18. The process according to claim 16 wherein in Step 2) the viscosity adjusting agent is added in the manufacturing tank containing the water for injection as first component and, once it is fully dissolved, the other excipients are added.

19. The process according to claim 16 wherein the sterilized bulk ophthalmic solution of Step 4) is filled in low density polyethylene (LDPE) ophthalmic primary containers.

* * * * *